United States Patent
Valaie

(10) Patent No.: US 8,163,001 B2
(45) Date of Patent: Apr. 24, 2012

(54) LOADING APPARATUS AND METHOD FOR EXPANDABLE INTRALUMINAL MEDICAL DEVICES

(75) Inventor: Arman Valaie, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 439 days.

(21) Appl. No.: 12/421,072

(22) Filed: Apr. 9, 2009

(65) Prior Publication Data

US 2009/0259287 A1    Oct. 15, 2009

Related U.S. Application Data

(60) Provisional application No. 61/043,492, filed on Apr. 9, 2008.

(51) Int. Cl.
*A61F 2/06* (2006.01)
(52) U.S. Cl. .......... 623/1.11; 29/282; 29/270; 29/272
(58) Field of Classification Search .......... 623/1.11, 623/1.12, 1.23; 29/235, 270, 272, 280, 282, 29/283.5
See application file for complete search history.

(56) References Cited

U.S. PATENT DOCUMENTS

| | | | |
|---|---|---|---|
| 5,486,193 A | 1/1996 | Bourne | |
| 5,725,519 A | 3/1998 | Penner | |
| 5,928,258 A | 7/1999 | Khan | |
| 6,051,002 A * | 4/2000 | Morales | 606/108 |
| 6,090,035 A | 7/2000 | Campbell | |
| 6,096,027 A | 8/2000 | Layne | |
| 6,149,680 A | 11/2000 | Shelso | |
| 6,471,718 B1 | 10/2002 | Staehle | |
| 6,640,412 B2 | 11/2003 | Iancea | |
| 6,689,123 B2 | 2/2004 | Pinchasik | |
| 6,823,576 B2 | 11/2004 | Austin | |
| 6,859,986 B2 | 3/2005 | Jackson | |
| 6,915,560 B2 | 7/2005 | Austin | |

(Continued)

FOREIGN PATENT DOCUMENTS

DE    19851846    5/2000

(Continued)

OTHER PUBLICATIONS

The International Searching Authority, International Search Report and the Written Opinion, Mar. 26, 2009, for International Application No., PCT/US2008/085510.

(Continued)

*Primary Examiner* — Gary Jackson
*Assistant Examiner* — Katrina Stransky
(74) *Attorney, Agent, or Firm* — Buchanan Nipper

(57) ABSTRACT

An apparatus for loading an expandable intraluminal medical device into a delivery device has a flexible main body with first and second rolled ends that enable the main body to alternatively adopt a substantially flat configuration that exposes a portion of the inner surface and a helical configuration that defines an interior chamber adapted to receive said expandable intraluminal medical device. An expandable intraluminal medical device is prepared for loading into a delivery device by placing the device on the main body of the loading apparatus while in the substantially flat configuration and then transforming the main body into the helical configuration. The medical device can then be compressed and forced out of the loading apparatus—and into a delivery device—by applying rotational and translational force to one end of the loading apparatus. Related kits and methods are also described.

20 Claims, 4 Drawing Sheets

U.S. PATENT DOCUMENTS

| | | |
|---|---|---|
| 7,402,171 B2 | 7/2008 | Osborne |
| 2001/0001128 A1* | 5/2001 | Holman et al. ............ 623/1.11 |
| 2002/0177899 A1 | 11/2002 | Eum |
| 2003/0055492 A1 | 3/2003 | Shaolian |
| 2003/0083730 A1 | 5/2003 | Stinson |
| 2003/0208254 A1 | 11/2003 | Shortt |
| 2003/0225445 A1 | 12/2003 | Derus |
| 2005/0246008 A1* | 11/2005 | Hogendijk et al. ......... 623/1.11 |
| 2006/0064152 A1 | 3/2006 | Olson |
| 2006/0183383 A1 | 8/2006 | Asmus et al. |
| 2006/0230592 A1 | 10/2006 | Heaney |
| 2007/0056346 A1 | 3/2007 | Spenser |
| 2007/0061009 A1 | 3/2007 | Spenser |
| 2007/0270931 A1 | 11/2007 | Leanna |
| 2007/0270932 A1 | 11/2007 | Headley |
| 2007/0270937 A1 | 11/2007 | Leanna |
| 2009/0143852 A1 | 6/2009 | Chambers et al. |
| 2009/0143857 A1 | 6/2009 | Melsheimer et al. |

FOREIGN PATENT DOCUMENTS

| | | |
|---|---|---|
| EP | 0657147 | 6/1995 |
| EP | 0938880 | 9/1999 |
| EP | 1362563 | 11/2003 |
| WO | 9959503 | 11/1999 |
| WO | 0040176 | 7/2000 |
| WO | 0249541 | 6/2002 |
| WO | 2007061801 | 5/2007 |

OTHER PUBLICATIONS

The International Searching Authority, International Search Report and the Written Opinion, Jul. 1, 2009, for International Application No. PCT/US2009/040026.

The International Bureau of WIPO, International Preliminary Report on Patentability, Jun. 17, 2010, for International Application No. PCT/US2008/085510.

The International Searching Authority, International Search Report and the Written Opinion, Apr. 2, 2009, for International Application No. PCT/US2008/085495.

The International Bureau of WIPO, International Preliminary Report on Patentability, Jun. 17, 2010, for International Application No. PCT/US2008/085495.

* cited by examiner

LOADING APPARATUS AND METHOD FOR EXPANDABLE INTRALUMINAL MEDICAL DEVICES

CROSS REFERENCE TO RELATED APPLICATION

This application claims priority to U.S. Provisional Application Ser. No. 61/043,492, filed on Apr. 9, 2008. The entire disclosure of this related application is hereby incorporated into this disclosure.

FIELD

The disclosure relates generally to the field of expandable intraluminal medical devices. More particularly, the disclosure relates to the field of expandable intraluminal medical devices that are loaded into a delivery device, such as a percutaneous delivery system, prior to deployment at a treatment site. Apparatuses for loading expandable intraluminal medical devices, such as stents, including coronary and other stents, stent graft devices, and prosthetic valves, such as prosthetic heart valves and prosthetic venous valves, into a delivery device are described. Kits and methods useful in the loading of expandable intraluminal medical devices are also described. Particular embodiments of the invention relate to the fields of expandable stents, such as coronary and other stents, stent-graft devices, and prosthetic valves, such as prosthetic heart valves and prosthetic venous valves.

BACKGROUND

A variety of expandable intraluminal medical devices have been developed over recent years. Stents, for example, are routinely used in several body lumens as a means for providing support to ailing vessels, such as coronary and non-coronary vessels. Stent-graft devices are frequently used as to provide support from within a body vessel and/or to exclude a portion of a vessel wall from the lumen of the vessel. Prosthetic valves, including heart and venous valve devices, that include expandable support frames have also been the focus of considerable development efforts over the last several years.

No matter the ultimate function of the device, expandable intraluminal medical devices are typically delivered to a point of treatment using a delivery system designed for percutaneous techniques. In a conventional procedure, a caregiver navigates the delivery system through one or more body vessels until the expandable intraluminal medical device, which is typically contained within a distal tip or portion of the delivery system, is positioned at or near the desired point of treatment. Next, the caregiver deploys the expandable intraluminal medical device from the delivery system, either by removing a constraining force for self-expandable devices or by providing an expansive force for balloon-expandable devices. Once deployment is complete, the delivery system is removed from the body vessel, leaving the expandable intraluminal medical device at the point of treatment.

During delivery, expandable intraluminal medical devices are maintained in a compressed, or reduced-diameter, configuration within the delivery system to ensure navigability of the delivery system through the body vessel. It is necessary, therefore, to compress the intraluminal medical device and place it within the delivery system at some point prior to use in the treatment procedure. For some devices, including some cardiac stents, this loading procedure can be conducted as part of the manufacturing process, i.e., prior to shipment to the treatment facility. For other devices, however, various concerns caution against loading the device at any point not immediately prior to delivery. For example, some tissue-based devices, such as prosthetic heart and venous valves, must be maintained in an appropriate fluid during all storage periods prior to use in a treatment procedure to ensure the integrity of the tissue component of the device. Furthermore, the effects of reduced-diameter storage of such tissue-based devices, particularly long-term storage, are not well-characterized and, as a result, are desirably avoided.

A loading procedure that is conducted immediately prior to treatment is subject to several concerns not considered critical for such procedures conducted outside of the treatment theater. For example, the loading procedure must not require bulky equipment that is difficult to use and/or inappropriate for the treatment theater. The procedure must be efficient and simple, and any materials or devices used in such a procedure should be easy to operate. A need exists, therefore, for a simple apparatus that facilitates loading of an expandable intraluminal medical device onto a delivery system. A need for improved methods of loading expandable intraluminal medical devices into delivery devices also exists.

BRIEF SUMMARY OF EXEMPLARY EMBODIMENTS

Apparatuses for loading expandable intraluminal medical devices into a delivery device are described. An apparatus according to one exemplary embodiment comprises a flexible main body having inner and outer surfaces, and first and second rolled ends. The main body is adapted to alternatively adopt a substantially flat configuration that exposes a portion of the inner surface and a helical configuration that defines an interior chamber adapted to receive the expandable intraluminal medical device desired to be loaded into the delivery device.

An apparatus according to another exemplary embodiment comprises a flexible main body having inner and outer surfaces and first and second rolled ends; a first cylindrical collar disposed around the first rolled end; a second cylindrical collar disposed around the second rolled end; a first handle partially disposed in the first cylindrical collar; and a second handle partially disposed in the second cylindrical collar. The main body is adapted to alternatively adopt a substantially flat configuration that exposes a portion of the inner surface and a helical configuration that defines an interior chamber for receiving said expandable intraluminal medical device by application of a rotational force to one of the first and second handles while maintaining the other of the first and second handles in a substantially stationary position.

Kits useful in the loading of an expandable intraluminal medical device into a delivery device are also described. A kit according to one exemplary embodiment comprises an expandable intraluminal medical device and a loading apparatus according to an embodiment of the invention.

Methods of loading expandable intraluminal medical devices into delivery devices are also described. An exemplary method comprises the steps of selecting an expandable intraluminal medical device and an appropriate delivery device defining an appropriate device chamber for containing the expandable intraluminal medical device; selecting a loading apparatus according to an embodiment of the invention; placing the loading apparatus in an open configuration to expose an inner surface of the main body; placing the expandable intraluminal medical device on the inner surface of the main body of the loading apparatus; placing the loading apparatus in a closed configuration to place the main body in a helical configuration and to dispose the expandable intraluminal medical device within an interior chamber formed by the helical configuration; applying a rotational force to an end of the loading apparatus to constrict the outer diameter of the helical configuration of the main body; and applying a substantially translational force to an end of the loading apparatus to advance the expandable intraluminal medical device along a lengthwise axis of the loading apparatus until the expandable intraluminal medical device is transferred from the interior chamber of the loading apparatus to the device chamber of the selected delivery device. Methods described herein are useful in loading expandable intraluminal medical devices into delivery devices either immediately prior to use in a treatment procedure, such as in the treatment theater by a treatment provider, or before the intraluminal medical device is within the treatment theater, such as in a manufacturing facility by manufacturing personnel.

Additional understanding of the claimed invention can be obtained with review of the following detailed description of exemplary embodiments and the appended drawings, which illustrate the described exemplary embodiments.

BRIEF DESCRIPTION OF THE DRAWINGS

FIG. 4A is a perspective view of an expandable intraluminal medical device and a loading apparatus according to an exemplary embodiment. The main body of the loading apparatus is in an open configuration and ready to receive the expandable intraluminal medical device.

FIG. 4B is an elevation view of the loading apparatus illustrated in FIG. 4A following loading of the expandable intraluminal medical device within the apparatus.

FIG. 4C is an elevation view of the loading apparatus illustrated in FIG. 4B following axial advancement of the second end of the apparatus.

DETAILED DESCRIPTION OF EXEMPLARY EMBODIMENTS

Figure 1:
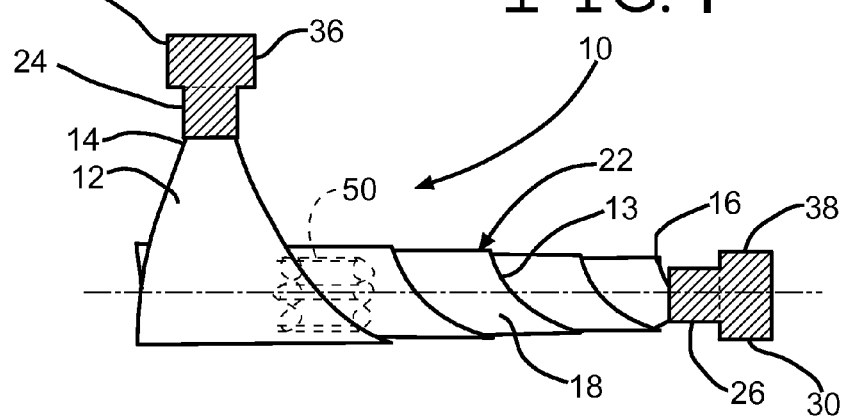
FIG. 1 is an elevation view of a loading apparatus according to a first exemplary embodiment. The main body of the apparatus is shown in a closed configuration.

The following detailed description and appended drawings describe and illustrate various exemplary embodiments of the invention. The description and drawings serve to enable one skilled in the art to make and use the invention, and are not intended to limit the scope of the invention or the protection sought in any manner.

FIGS. 1 through 3, 4A, 4B, and 4C illustrate a loading apparatus 10 according to a first exemplary embodiment. The loading apparatus 10 includes a main body 12 having first 14 and second 16 ends and outer 18 and inner 20 surfaces. A first collar 24 is disposed on the first end 14 of the apparatus 10, and a second collar 26 is disposed on the second end 16. A first handle 28 is attached to the first end 14 and a second handle 30 is attached to the second end 16 of the apparatus 10.

Figure 2:
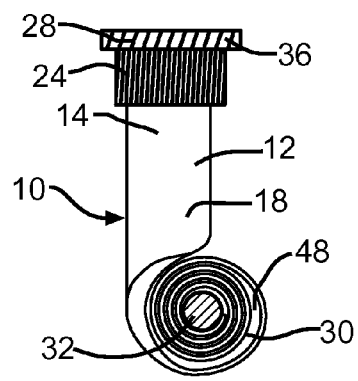
FIG. 2 is an end view of the loading apparatus according to the first exemplary embodiment.
Figure 3:
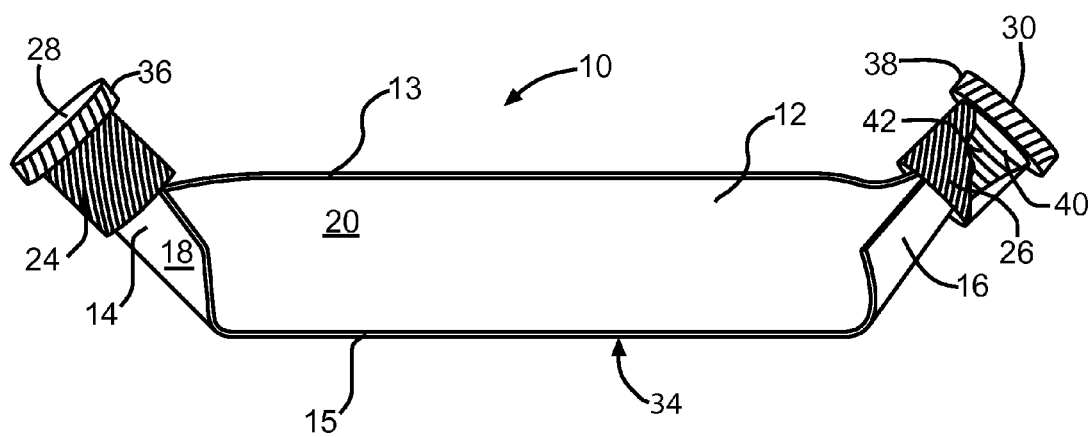
FIG. 3 is a perspective view, partially broken away, of the loading apparatus according to the first exemplary embodiment. The main body of the apparatus is shown in an open configuration.

FIGS. 1 and 2 illustrate the apparatus 10 in a closed configuration in which the main body 12 is coiled on itself to form a helical configuration 22 and define an interior chamber. In this configuration, the main body 12 is coiled upon itself such that a substantial portion of the inner surface 20 is disposed adjacent, and substantially in contact with, the outer surface 18. The helical configuration 22 is also characterized by the helical path defined by the longer edge 13 of the rectangular main body 12. The opposite edge 15 also defines a helical path in this configuration, although this edge 15 is not visible in FIG. 1. FIG. 3 illustrates the apparatus 10 in an open configuration in which the main body 12 has been uncoiled to form a substantially flat configuration 34 and to substantially eliminate the interior chamber 32 provided by the closed configuration. In this configuration, the inner surface 20 is disposed opposite the outer surface 18 and is substantially free of contact with the outer surface. As illustrated in FIG. 3, the flat configuration 34 can include an absence of contact between the outer 18 and inner 20 surfaces.

As illustrated in FIG. 1 and as described in detail below, an expandable intraluminal medical device 50 is placed in the interior chamber 32 of the apparatus 10 during use.

The main body 12 can be formed of any suitable material. The material selected for a specific loading apparatus according to an embodiment of the invention will depend on various considerations, including the nature of the expandable intraluminal medical device with which the apparatus is intended to be used. The material selected should be sufficiently flexible to allow the apparatus to alternatively adopt the flat 34 and helical 22 configurations with a simple holding and twisting of the handles 28, 30, as described more fully below. Furthermore, the material should have a sufficient coefficient of friction with respect to itself to allow portions of the main body 12 to slide relative to each other during axial advancement of the second end 16 of the apparatus 10, which occurs during operation of the apparatus 10. For example, as described above, a substantial portion of the inner surface 20 is disposed adjacent a substantial portion of the outer surface 18 when the apparatus 10 is in the helical configuration. Portions of the inner 20 and outer 18 surfaces contact each other in this configuration. During axial advancement of the second end 16, friction is generated by this contact and movement. A material that provides desirable frictional properties during this movement is considered advantageous. Examples of suitable materials include, but are not limited to, various plastic and metal materials. VRTS, polypropylene, and polyethylene are considered suitable materials, as are stainless steel and aluminum. Super polished stainless steel and aluminum also are considered suitable.

It is noted that the main body 12 can be a composite of two materials, providing different surfaces for the inner 20 and outer 18 surfaces. Transparent or translucent materials, or materials with sections that are transparent or translucent, can also be used and are considered advantageous in embodiments in which it is considered advantageous and/or desirable to allow a user to verify the presence of the expandable intraluminal medical device within the loading apparatus prior to use, or to track movement and/or the configuration of the device during a loading procedure. Furthermore, the main body 12 can comprise a section of material having one or both sides coated with a lubricious coating that reduces friction generated by relative movement of the sides with each other.

The main body 12 can be trained to resume one or both of the helical 22 and flat 34 configurations. For example, materials exhibiting shape memory properties, such as nitinol and other shape memory materials known in the art, can be used. In these embodiments, the main body 12 can be trained to assume one configuration, such as the helical configuration 22, once an appropriate configuration change trigger is achieved, such as a transition temperature.

Essentially any material that provides a suitable surface can be used for the main body 12. The material should be selected such that the surface of the main body 12 does not catch the ends of the expandable intraluminal medical device 50 as it is forced through the apparatus 10, and have appropriate surface properties that allow the device 50 to be slideably advanced through the interior of the apparatus 10 during use. A skilled artisan will be able to select an appropriate material for use in the main body 12 in an apparatus 10 according to a particular embodiment of the invention based on these and other considerations, including the nature, size and configuration of the expandable intraluminal medical device 50.

In the embodiment illustrated in FIGS. 1 through 3, the main body 12 comprises a substantially rectangular section of material. The size and shape selected for a specific loading apparatus according to an embodiment of the invention will depend on various considerations, including the size and configuration of the expandable intraluminal medical device with which the apparatus is intended to be used. As best illustrated in FIG. 1, the size and shape of the main body 12 should be selected to allow the expandable intraluminal medical device 50 to be placed on the inner surface 20 when the main body 12 is in the flat configuration 34 and to allow the expandable intraluminal medical device 50 to be contained within the interior chamber 32 when the main body 12 is in the helical configuration 22. The inventors have determined that, for a loading apparatus intended to be used with tissue-based venous valves, a section of VRTS material that is approximately 12 mm long, approximately 2.5 mm wide, and approximately 0.0025" thick provides an advantageous configuration.

As best illustrated in FIG. 3, each of the opposing first 14 and second 16 ends of the main body 12 comprises a rolled end. As used herein, the term "rolled end" refers to an end of a substantially flat section of material in which opposing sides or corners are brought toward each other and fixed in position relative to each other. The opposing sides or corners can, but need not, be placed in contact with each other. Also, a "rolled end" can, but need not, include a curvilinear portion—a crease or fold in the material, between the opposing sides or corners, is acceptable and may be advantageous in certain embodiments.

In the first exemplary embodiment, illustrated in FIGS. 1 through 3, 4A, 4B and 4C, each of the ends 14, 16 is individually collected into respective first 24 and second 26 collars. The appropriate collar 24, 26 is placed over at least a portion of the appropriate rolled end 14, 16. The collars 24, 26 are advantageously secured to the rolled ends 14, 16 using any suitable means for securing materials to each other, including mechanical bonds, such as those formed by crimping, and chemical bonds, such as those formed by the use of adhesives and annealing treatments. A separate attachment member, such as a wire thread, staple, or other suitable means for securing materials to each other, can also be used to secure the collars 24, 26 to the ends 14, 16 of the main body 12.

As used herein, the term "collar" refers to a member that partially or completely extends around a portion of one end 14, 16 of the main body 12. The collars 24, 26 can have any suitable configuration, size, shape, and/or form that achieves this structural arrangement. In the illustrated embodiment, each of the collars 24, 26 comprises a cylindrical member. This configuration of the collars 24, 26 is considered advantageous at least because it allows the collars 24, 26 to receive the rolled ends 14, 16 of the main body 12, as described above, in one end and also allows for the receipt of a portion of an optional handle member, as described in more detail below. Any other suitable configuration can be used for the collars 24, 26, though, and a skilled artisan will be able to select appropriate collars based on various considerations, including the nature of the material selected for the main body, the desired ruggedness of the attachment between the collars and the ends of the main body, and others. Examples of other suitable configurations for the collars include a cylindrical member with a longitudinal slit (e.g., a c-shaped member) and a coil.

As noted above, the collars 24, 26 can serve the additional function of maintaining the rolled ends 14, 16 in their configuration, such as by an attachment of each side and/or corner of the rolled end 14, 16 to a portion of the collar 24, 26. In these embodiments, the sides and/or corners of the rolled ends 14, 16 can be attached to each other through appropriate means, or can be free of attachment to each other. It is considered advantageous, but optional, to include attachments both between the sides and/or corners of the rolled ends 14, 16 and between the collars 24, 26 and the ends 14, 16.

The first handle 28 provides a surface 36 that can be gripped by a user during use of the loading apparatus 10. Similarly, the second handle 30 provides a surface 38 suitable for gripping. Any suitable surface can be used and the surface selected for a loading apparatus according to a particular embodiment will depend on various considerations, including the nature of the environment within which the apparatus 10 is intended to be used. For example, the surfaces 36, 38 of the apparatus illustrated in FIGS. 1 through 3 each comprise a ridged circumferential surface, which may be advantageous for use in environments in which users are likely to be wearing gloves. The inclusion of the ridged surface is considered advantageous at least because it provides a suitable gripping surface during application of a torque on one end of the apparatus, as described in more detail below. Suitable alternative surfaces include smooth surfaces and surfaces coated with a coating, such as a rubber overgrip or an adhesive with acceptable tack characteristics.

The surfaces 36, 38 can be the same or different. The handle 30 attached to the second end 16 of the loading apparatus 10, i.e., the end to which the torque is applied during a loading procedure, as described in more detail below, advantageously includes a suitable gripping surface, such as that provided by the ridged circumferential surface 38 illustrated in FIGS. 1 through 3.

As best illustrated in FIG. 3, the handle 30 comprises a thumb screw having a body portion 40 disposed in the appropriate collar 24, 26 and the gripping surface 36, 38 disposed external to the collar 24, 26. The body portion 40 of the screw advantageously defines a helical ridge 42 on its external surface. The inclusion of the helical ridge 42 enhances the attachment between the collar 26 and main body 10, increasing the overall ruggedness of the loading apparatus 10.

While considered advantageous, it is noted that one or both of the handles 28, 30 can be omitted if the collar(s) 24, 26 and/or ends 14, 16 of the main body 12 provide an acceptable surface for applying the necessary torque to operate the loading apparatus 10.

Figure 4A:
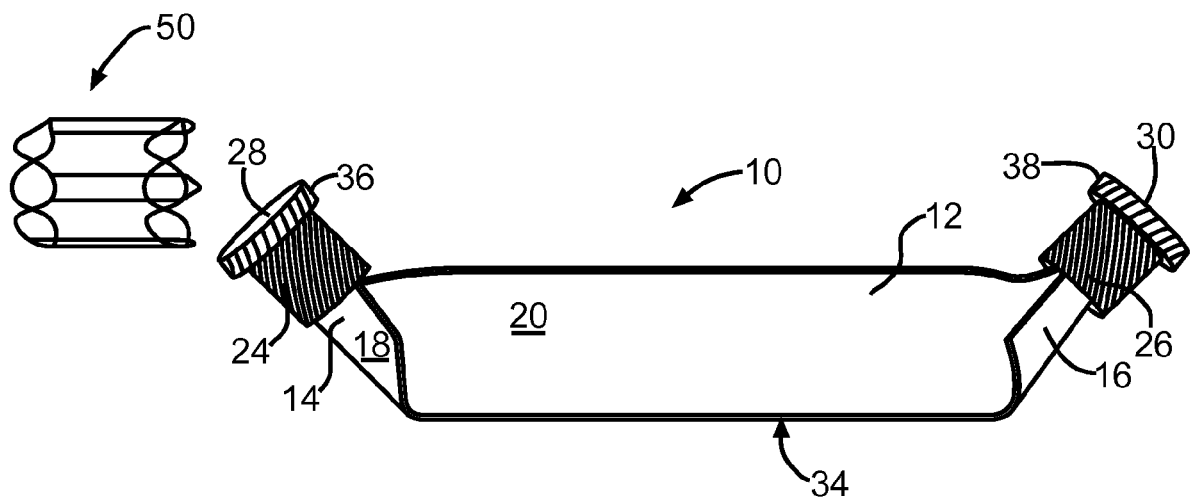
FIGS. 4A through 4C illustrate use of a loading apparatus according to an exemplary embodiment.
Figure 4B:
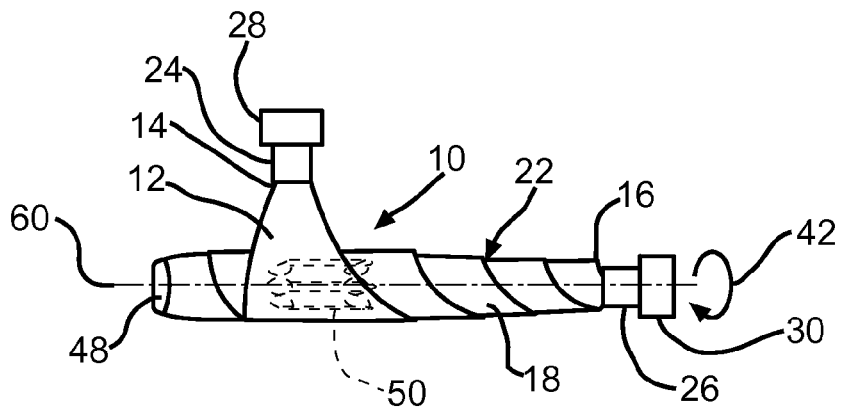
Figure 4C:
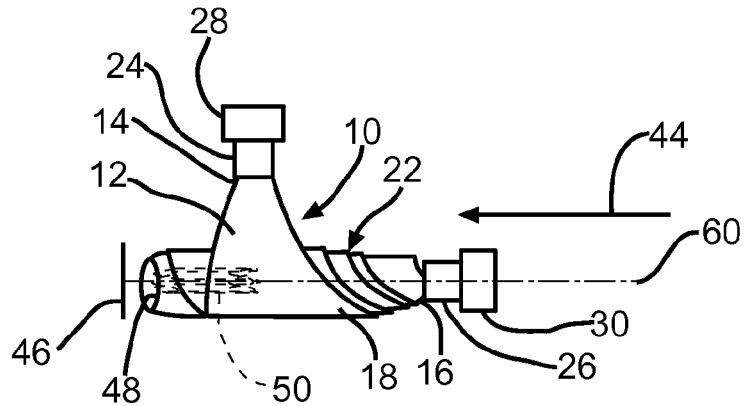

FIGS. 4A through 4C illustrate use of the loading apparatus 10 according to the first exemplary embodiment of the invention.

In FIG. 4A, the loading apparatus is in the open configuration with the main body 12 in its flat configuration 34. This configuration is achieved by applying torque to the second handle 30 to unwind the helical configuration 22 of the main body 12 when the loading apparatus 10 is in its closed configuration. Holding the first handle 28 and maintaining it in a substantially fixed position while applying torque to the second handle 30 facilitates the change from the closed to the open configurations of the loading apparatus 10. The expandable intraluminal medical device 50 is not associated with the loading apparatus in FIG. 4A.

In FIG. 4B, the expandable intraluminal medical device 50 is positioned within the interior chamber 32 defined by the main body 12 in the helical configuration 22. To achieve this positioning, the expandable intraluminal medical device 50 is placed on the inner surface 20 of the main body 12 while in the flat configuration 34 illustrated in FIG. 4A. A torque is then applied to the second handle 30 while holding the first handle 28 to place the main body in the helical configuration 22, essentially wrapping the helix formed by the main body 12 around the external surface of the expandable intraluminal medical device 50. As illustrated in FIG. 4B, the torque is advantageously applied by rotating the second handle 30 about a lengthwise axis 60 of the apparatus 10 in the direction symbolized by arrow 42.

At this point, the expandable intraluminal medical device 50 is contained within the interior chamber 32 of the loading apparatus 10 and is ready for transfer to a suitable delivery device. To achieve such transfer, a rotational force is applied to the second handle 30 to compress the outer diameter 46 of the helical configuration 22 of the main body 12. The rotational force is applied until the outer diameter 46 reaches a sufficient size to allow the expandable intraluminal medical device 50 to enter an opening of a selected delivery device. For example, the force can be applied until the outer diameter 46 is slightly less than an inner diameter of a constraining portion of a delivery system into which the expandable intraluminal medical device 50 is being loaded, such as an outer sheath member.

At the same time as or following application of the rotational force, the second handle 30 and, as a result, the expandable intraluminal medical device 50, is advanced along a lengthwise axis 60 of the apparatus 10 by applying a substantially translational force to the second handle 30 in the direction symbolized by arrow 44. The application of such a force causes the overall length of the helical configuration 22 to be reduced. Further constriction of the outer diameter 46 may also result from such force. Ultimately, the expandable intraluminal medical device 50 is forced out of the opening 48 formed by the helical configuration 22 of the main body 12 between the first 14 and second 16 ends.

It may be necessary to apply the translational and/or torque forces to the second handle 30 two or more times to achieve complete transfer of the expandable intraluminal medical device 50 to the selected delivery device. This repeated application of one or both forces can be accomplished by repeatedly pushing and/or twisting the second handle 30 and releasing the handle 30 until transfer is achieved.

After transfer is complete, the loading apparatus 10 can simply be retracted from the selected delivery device. Rotational and/or translational forces applied in the reverse direction of those indicated by arrows 44 may facilitate retraction of the apparatus 10. As all materials of the apparatus 10 are advantageously made of plastic or other inexpensive materials, the apparatus can simply be discarded or recycled following retraction.

It is noted that the loading apparatus 10 can be used with any suitable expandable intraluminal medical device 50. The size, type and configuration of the expandable intraluminal medical device 50 used with a loading apparatus 10 according to a particular embodiment of the invention will, of course, depend on the nature of the treatment procedure being conducted. The user of the apparatus 10 can select an appropriate expandable intraluminal medical device 50 based on the treatment objectives. Kits that include a paired loading apparatus and expandable intraluminal medical device 50 are also provided, as described in more detail below.

The loading apparatus 10 is particularly well-suited for use with expandable intraluminal medical devices for which loading the device into a selected delivery device immediately prior to a treatment procedure is recommended or otherwise considered desirable. Examples of such expandable intraluminal medical devices include stents with biologically-active coatings, stents with attached grafts, including grafts of biological origin, and tissue-based prosthetic valve devices, such as prosthetic heart valve and prosthetic venous valves that include one or more section of tissue, tissue-derived material, or other flexible material.

Figure 5:
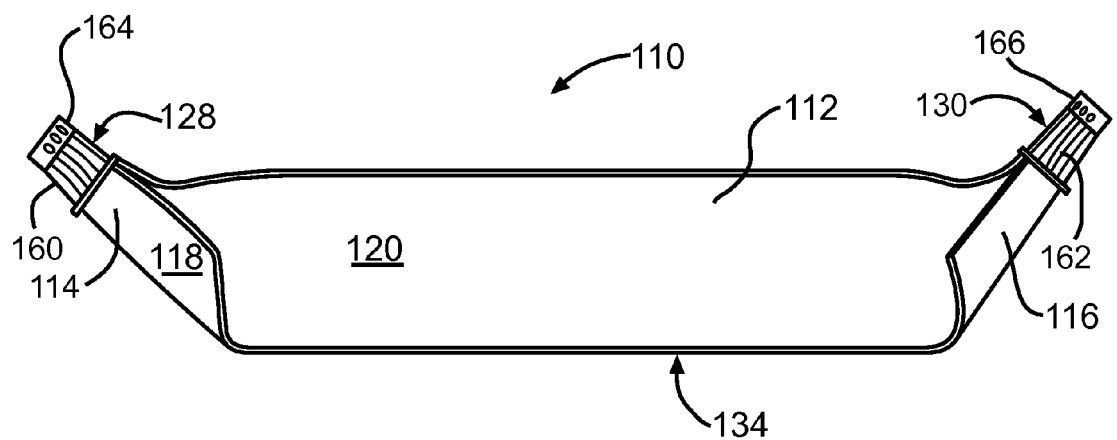
FIG. 5 is a perspective view of a loading apparatus according to a second exemplary embodiment.

FIG. 5 illustrates a loading apparatus 110 according to a second exemplary embodiment of the invention. The loading apparatus 110 according to this embodiment is similar to the apparatus 10 according to the first exemplary embodiment and illustrated in FIGS. 1 through 3, 4A, 4B, and 4C, except as described below. Thus, the loading apparatus 110 includes a main body 112 having first 114 and second 116 ends and outer 118 and inner 120 surfaces. The apparatus 100 is illustrated in the open configuration, with the main body 112 in the substantially flat configuration 134.

In this embodiment, the first 128 and second 130 handles comprise a treated portion of the first 114 and second 116 ends of the main body 112, respectively. The first handle 128 comprises two portions of the first end 114 that have been attached to each other, such as by an annealing process, formation of a mechanical bond, by application of a suitable adhesive, or by the formation of any other suitable attachment. A surface 164 with suitable gripping properties, such as inclusion of raised ridges or bumps, is included at the terminal end of the first handle 128. Similarly, the second handle 130 comprises two portions of the second end 116 that have been attached to each other in a similar or different fashion. A surface 166 with suitable gripping properties is also provided. The surfaces 164, 166 advantageously comprise sections of the outer surface 118 of the main body 112, but can also comprise separately attached members, coatings, and the like.

The loading apparatus 110 according to this embodiment is used in a similar manner as the apparatus 10 according to the first exemplary embodiment and illustrated in FIGS. 1 through 3, 4A, 4B, and 4C. Thus, a selected expandable intraluminal medical device is placed on the inner surface 120 of the main body 112 while in the flat configuration 134. A torque is then applied to the second handle 130 while holding the first handle 128 to place the main body 112 in the helical configuration (not illustrated), essentially wrapping the helix formed by the main body 112 around the external surface of the expandable intraluminal medical device (not illustrated).

In another alternative embodiment, the loading apparatus is not able to adopt the open configuration in which the main body is in the flat configuration. This embodiment is similar to the previously described embodiment except that the main body cannot be unrolled to adopt the flat configuration. The material of the main body can have structural properties that prevent such unrolling or the main body can be fixed in the helical configuration, such as by adhesives, coatings over the external surface, mechanical restrictions on the apparatus, and the like. For these embodiments, the main body must preserve the ability to constrict upon the application of a rotational force of one handle to achieve the desired compression unless the apparatus is supplied in a compressed configuration.

Figure 6:
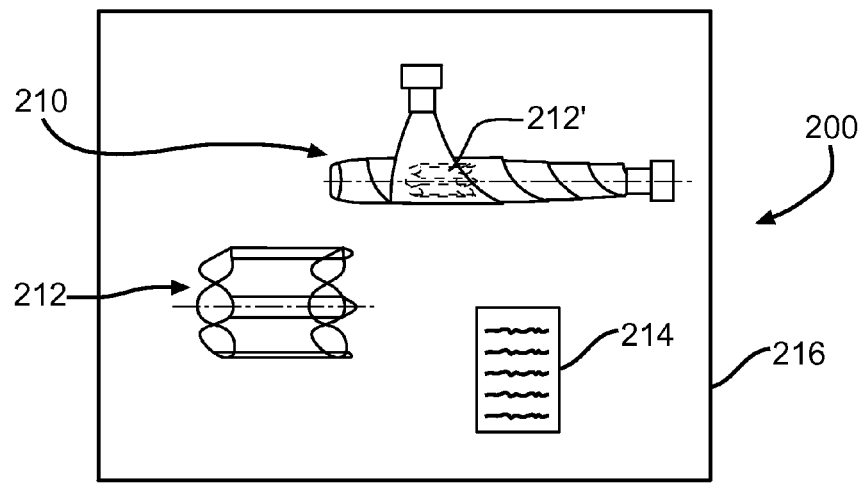
FIG. 6 is a schematic of a kit according to an exemplary embodiment.

FIG. 6 illustrates a kit 200 according to an exemplary embodiment. Kits according to the invention are useful in a variety of clinical situations in which loading of an expandable intraluminal medical device immediately prior to treatment is recommended or otherwise desirable, and in other clinical situations in which loading after manufacturing is desired.

The kit 200 includes a loading apparatus 210 according to an embodiment of the invention and an expandable intraluminal medical device 212. Optional instructions for use of the loading apparatus 210 and/or the expandable intraluminal medical device 212 can also be included in the kit 200.

The loading apparatus 210 and expandable intraluminal medical device 212 are advantageously matched so as to be acceptable for use with each other. Thus, the expandable intraluminal medical device 212 advantageously is adapted for being disposed on the inner surface of the loading apparatus 210 when the main body is in the flat configuration, as described above, and is adapted for being wrapped within the helical configuration of the main body when the loading apparatus 210 is placed in its closed configuration. Also, the main body of the loading apparatus advantageously is composed of a material suitable for use with the expandable intraluminal medical device 212, including any attached components, such as graft and/or tissue components.

The kit 200 can optionally include a delivery device suitable for use with the expandable intraluminal medical device 212 and the loading apparatus 210. Examples of suitable delivery devices include percutaneous delivery systems comprising a dilator disposed within a surrounding sheath and defining a device chamber into which an intraluminal medical device can be disposed.

It is noted that, while the kit 200 is illustrated as having the expandable intraluminal medical device 212 packaged in the container 216 external to the loading apparatus 210, the expandable intraluminal medical device can, alternatively, be packaged in the kit 200 internal to the loading apparatus, i.e., within the interior chamber formed by the helical configuration of the main body of the loading apparatus 210. This is illustrated in FIG. 6 with reference number 212. This structural arrangement for the kit may be desirable for expandable intraluminal medical devices for which it is considered desirable or advantageous to minimize handling, such as during loading procedures. In these embodiments, a main body of the loading apparatus 210 that is formed of transparent or translucent material that allows a user to verify the presence of the expandable intraluminal medical device within the loading apparatus 210 is considered advantageous. Also, in these embodiments, the loading apparatus need not be able to adopt the open configuration, although this is certainly acceptable.

The kit 200 advantageously includes a container 216 within which the loading apparatus 210, expandable intraluminal medical device 212, and optional instructions for use can be disposed. Any suitable container can be used, including those formed of disposable and/or recyclable cardboard and plastic materials.

Figure 7:
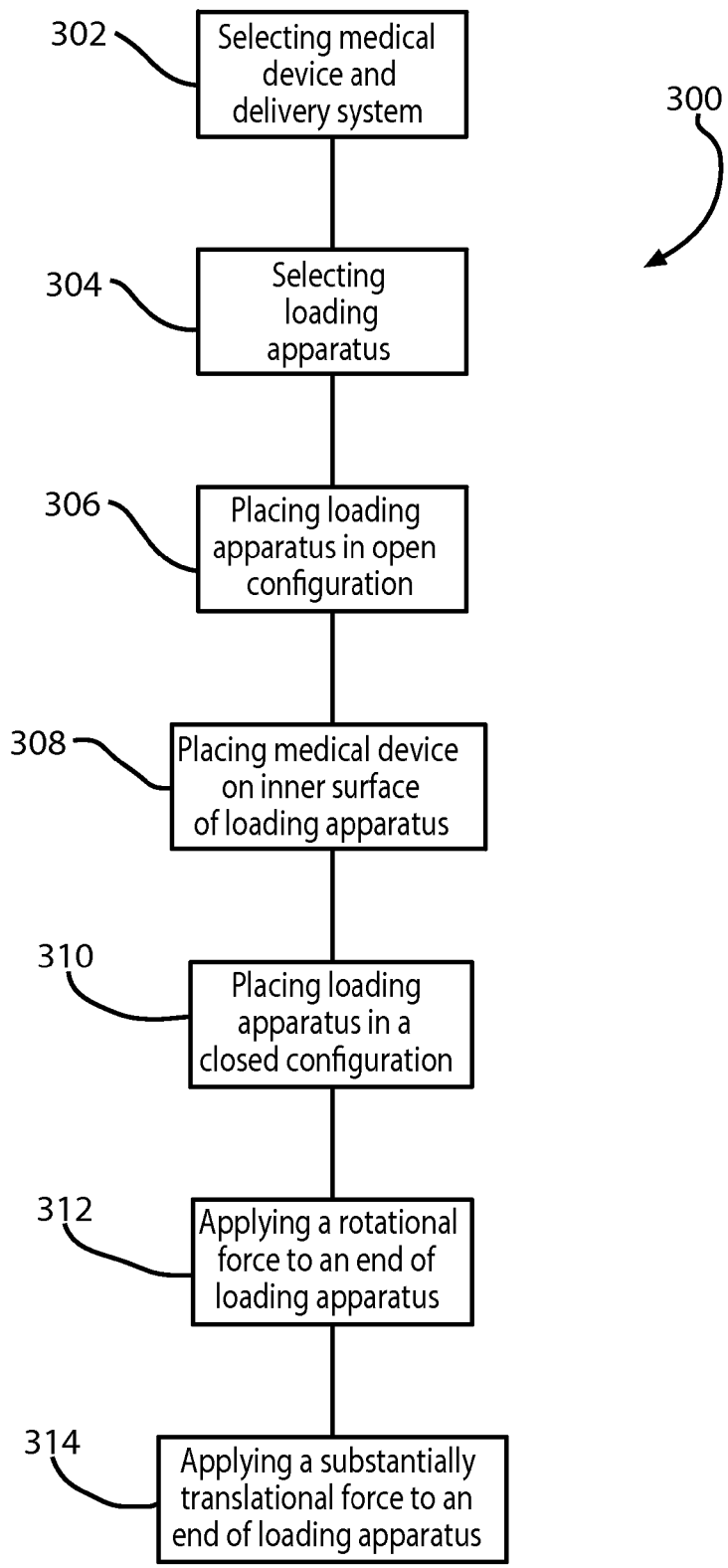
FIG. 7 is a flowchart illustrating an exemplary method of loading an expandable intraluminal medical device into a delivery device.

FIG. 7 illustrates a flowchart of an exemplary method 300 of loading an expandable intraluminal medical device into a delivery device. A first step 302 comprises selecting an expandable intraluminal medical device and an appropriate delivery device providing an appropriate device chamber for containing the expandable intraluminal medical device. Another step 304 comprises selecting a loading apparatus according to an embodiment of the invention. The loading apparatus can be one of the embodiments described and/or illustrated herein or a loading apparatus according to any other embodiment of the invention. Another step 306 comprises placing the loading apparatus in an open configuration to expose an inner surface of the main body. This can be accomplished by applying torque to one end of the apparatus as described above. Another step 308 comprises placing the expandable intraluminal medical device on the inner surface of the main body of the loading apparatus. Another step 310 comprises placing the loading apparatus in a closed configuration to place the main body in a helical configuration and to dispose the expandable intraluminal medical device within an interior chamber formed by the helical configuration. Another step 312 comprises applying a rotational force to an end of the loading apparatus to constrict the outer diameter of the helical configuration of the main body. Another step 314 comprises applying a substantially translational force to an end of the loading apparatus to advance the expandable intraluminal medical device along a lengthwise axis of the loading apparatus until the expandable intraluminal medical device is transferred from the interior chamber of the loading apparatus to a device chamber of the selected delivery device.

The steps of applying a rotational force to an end of the loading apparatus to constrict the outer diameter of the helical configuration of the main body and applying a substantially translational force to an end of the loading apparatus to advance the expandable intraluminal medical device along a lengthwise axis of the loading apparatus can be conducted separately or together. Further, these steps can be repeated, individually or together, until the expandable intraluminal medical device is transferred from the interior chamber of the loading apparatus to a device chamber of the selected delivery device. It is noted that, prior to the step of applying a substantially translational force to an end of the loading apparatus 314, the loading apparatus should be positioned adjacent the delivery system such that an opening of the loading apparatus is adjacent an opening of the delivery device. For example, the opening of the loading apparatus that is opposite the end to which the translational force is applied can be positioned adjacent a distal end and opening of the sheath of the delivery system. Contact, such as abutting contact, between the loading apparatus and sheath is considered advantageous.

In another exemplary method, a loading apparatus within which an expandable intraluminal device is already positioned is selected. In these methods, the step of selecting a medical device and selecting a loading apparatus are one and the same, and the steps of placing the loading apparatus in an open configuration, placing the medical device on the inner surface of the loading apparatus, and placing the loading apparatus in a closed configuration are eliminated. Furthermore, the step of applying a rotational force to an end of the loading apparatus is optional; its inclusion will depend on the nature of the main body as described above. Otherwise, this exemplary method is the same as the method described above.

It is noted that, in addition to use with delivery systems, the loading apparatus, kits and methods described herein can be used in the loading of an expandable intraluminal medical device into other apparatuses, such as storage vessels, research equipment, sterilization containers, and other suitable apparatuses adapted to contain an expandable intraluminal medical device in a compressed or reduced-diameter configuration.

The embodiments described and illustrated herein represent examples of the invention, and are not intended to limit the scope of the invention or the protection sought in any manner. Rather, they serve only to aid those skilled in the art to make and use the invention.

What is claimed is:

1. An apparatus for loading an expandable intraluminal medical device into a delivery device, comprising:
   a flexible main body having inner and outer surfaces, first and second opposing edges and first and second rolled ends, the main body adapted to alternatively adopt a substantially flat configuration that exposes a portion of the inner surface and a helical configuration in which the main body is coiled upon itself such that each of the first and second opposing edges defines a helical path, a substantial portion of the inner surface is disposed adjacent to and in contact with the outer surface, and such that the helical path defined by one of the first and second opposing edges is free of contact with the inner surface, the helical configuration defining an interior chamber adapted to receive said expandable intraluminal medical device;
   wherein one of the first and second rolled ends is disposed on a lengthwise axis of the apparatus and the other of the first and second rolled ends is disposed on a different axis that transects the lengthwise axis when the main body is in the helical configuration.

2. The apparatus of claim 1, further comprising a collar disposed around at least one of the first and second rolled ends.

3. The apparatus of claim 1, further comprising a first collar disposed around the first rolled end and a second collar disposed around the second rolled end.

4. The apparatus of claim 1, further comprising a handle associated with at least one of the first and second rolled ends.

5. The apparatus of claim 1, further comprising a first handle associate with the first rolled end and a second handle associated with the second rolled end.

6. The apparatus of claim 2, wherein the collar comprises a cylinder.

7. The apparatus of claim 6, further comprising a handle having at least a portion disposed within the collar.

8. The apparatus of claim 7, wherein the portion disposed within the collar defines a helical ridge.

9. The apparatus of claim 1, wherein at least one of the first and second ends includes first and second portions of the main body attached to each other.

10. The apparatus of claim 9, wherein the first and second portions of the main body are annealed to each other.

11. The apparatus of claim 1, wherein the main body is formed of a plastic or metal material.

12. An apparatus for loading an expandable intraluminal medical device into a delivery device, comprising:
    a flexible main body adapted to alternatively adopt a substantially flat configuration and a helical configuration, the main body having inner and outer surfaces, first and second opposing edges, and first and second rolled ends, one of the first and second rolled ends disposed on a lengthwise axis of the apparatus and the other of the first and second rolled ends disposed on a different axis that transects the lengthwise axis when the main body is in the helical configuration;
    a first cylindrical collar disposed around the first rolled end;
    a second cylindrical collar disposed around the second rolled end;
    a first handle partially disposed in the first cylindrical collar; and
    a second handle partially disposed in the second cylindrical collar;
    wherein the main body is adapted to alternatively adopt the substantially flat configuration that exposes a portion of the inner surface and the helical configuration in which the main body is coiled upon itself such that each of the first and second opposing edges defines a helical path, a substantial portion of the inner surface is disposed adjacent to and in contact with the outer surface, and such that the helical path defined by one of the first and second opposing edges is free of contact with the inner surface, the helical configuration defining an interior chamber for receiving said expandable intraluminal medical device by application of a rotational force to one of the first and second handles while maintaining the other of the first and second handles in a substantially stationary position.

13. The apparatus of claim 12, further comprising:
    a first fastener connecting the first end, first cylindrical collar, and first handle; and
    a second fastener connecting the second end, second cylindrical collar, and second handle.

14. The apparatus of claim 12, wherein at least one of the first and second ends includes first and second portions of the main body attached to each other.

15. The apparatus of claim 12, wherein each of the first and second ends includes first and second portions of the main body attached to each other.

16. The apparatus of claim 12, wherein the main body is formed of a plastic or metal material.

17. A method of loading an expandable intraluminal medical device into a delivery device, said method comprising the steps of:
    selecting an expandable intraluminal medical device and an appropriate delivery device defining an appropriate device chamber for containing the expandable intraluminal medical device;
    selecting a loading apparatus comprising a flexible main body having inner and outer surfaces, first and second opposing edges, and first and second rolled ends, the main body adapted to alternatively adopt a substantially flat configuration that exposes a portion of the inner surface and a helical configuration in which the main body is coiled upon itself such that each of the first and second opposing edges defines a helical path, the helical path defined by one of the first and second opposing edges is free of contact with the inner surface, and such that one of the first and second rolled ends is disposed on a lengthwise axis of the apparatus and the other of the first and second rolled ends is disposed on a different axis that transects the lengthwise axis, the helical configuration defining an interior chamber adapted to receive said expandable intraluminal medical device;
    placing the loading apparatus in an open configuration to expose an inner surface of the main body;
    placing the expandable intraluminal medical device on the inner surface of the main body of the loading apparatus;
    placing the loading apparatus in a closed configuration to place the main body in a helical configuration and to dispose the expandable intraluminal medical device within an interior chamber formed by the helical configuration;

applying a rotational force to an end of the loading apparatus to constrict the outer diameter of the helical configuration of the main body; and applying a substantially translational force to an end of the loading apparatus to advance the expandable intraluminal medical device along a lengthwise axis of the loading apparatus until the expandable intraluminal medical device is transferred from the interior chamber of the loading apparatus to the device chamber of the selected delivery device.

18. The method of claim 17, wherein the steps of applying a rotational force to an end of the loading apparatus and applying a substantially translational force to an end of the loading apparatus are conducted sequentially.

19. The method of claim 17, wherein the steps of applying a rotational force to an end of the loading apparatus and applying a substantially translational force to an end of the loading apparatus are conducted simultaneously.

20. The method of claim 17, wherein at least one of the steps of applying a rotational force to an end of the loading apparatus and applying a substantially translational force to an end of the loading apparatus is repeated at least once.

* * * * *